Jan. 15, 1963 W. H. KEMPLE Plant Pat. 2,219
ROSE PLANT
Filed March 15, 1962
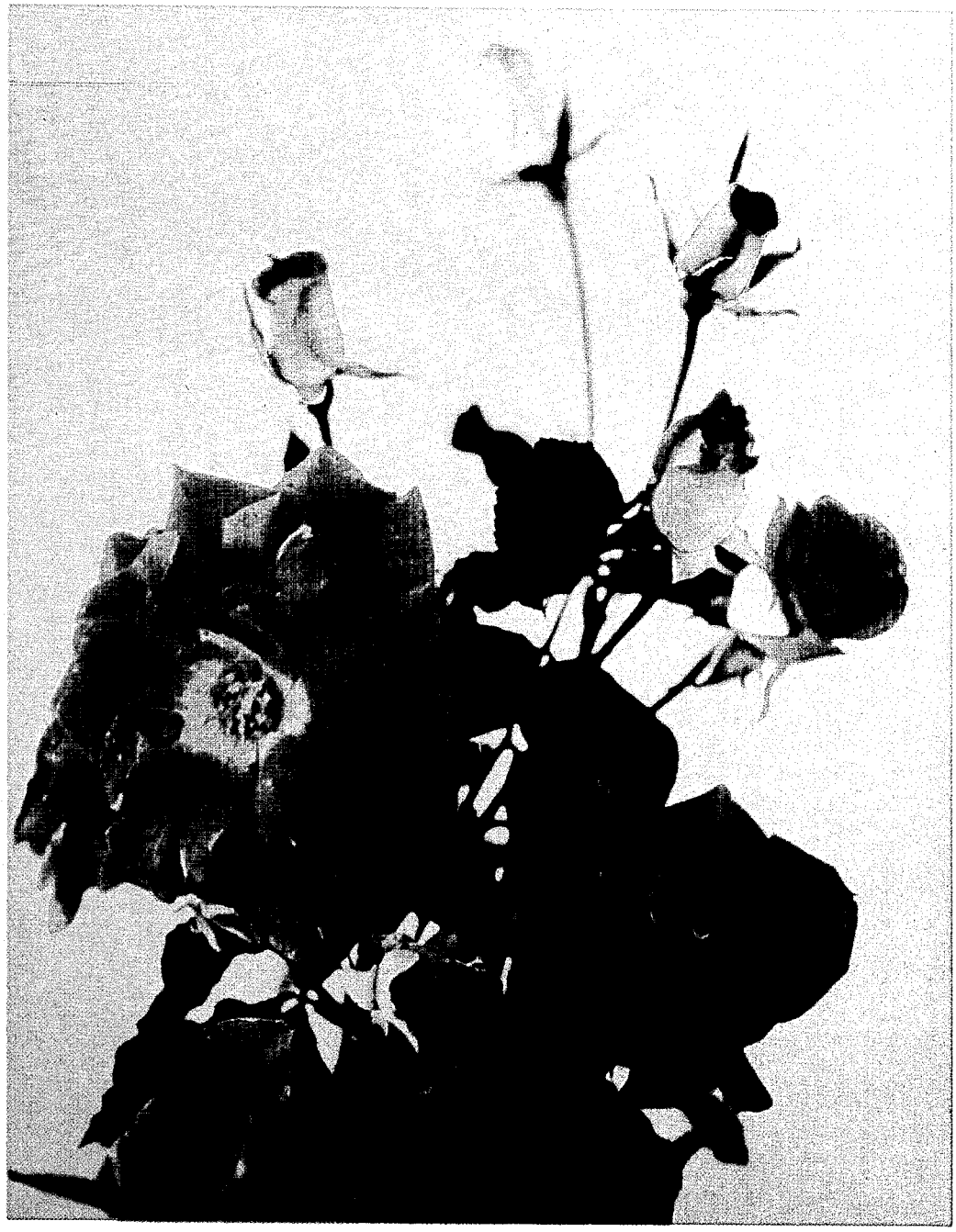
INVENTOR
William H. Kemple
BY Robb & Robb
ATTORNEYS United States Patent Office Plant Pat. 2,219
Patented Jan. 15, 1963

2,219
ROSE PLANT

William H. Kemple, San Diego, Calif., assignor to J. H. van Barneveld, La Habra, Calif.

Filed Mar. 15, 1962, Ser. No. 180,062
1 Claim. (Cl. 47—61)

The present invention relates to a new and distinct variety of rose plant of the floribunda class, which was originated by me by crossing the variety "Baby Chateau" (unpatented) with the variety "Contrast" (unpatented).

As the result of this breeding, I have produced a new rose variety which is endowed with the following unique combination of commercially desirable characteristics which distinguish the same from its parents, as well as from all other varieties of which I am aware:

(1) Good bush form which requires no shaping or pruning;

(2) Shiny, varnished, deep green and clean foliage which completely clothes the plant to present a clean and attractive appearance;

(3) Substantially continuous flower production throughout the entire growing season, even in comparatively cold geographical areas, such as the States of Illinois and Wyoming, and elsewhere;

(4) Hardy and long-lasting flowers which drop off cleanly before creating an unsightly appearance;

(5) A distinctive and attractive vermilion-scarlet, with silvery white reverse general color tonality of the flowers which is unique in the class of floribunda roses, and has never been achieved, to my knowledge, even in other classes;

(6) Strong and pleasing fragrance of the flowers, which is also unusual in floribunda roses, as well as seldom achieved in roses of other classes; and (7) Good resistance to mildew, thrips and aphis infestations.

Asexual reproduction of my new variety as performed by budding at both Cucamonga and Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Nickerson's Color Fan, published by Munsell Color Company, Inc., of Baltimore, Maryland, except where general color terms of ordinary dictionary significance are obvious.

Type: Hardy; dwarf; bush; greenhouse and outdoor; seedling; for cut flowers and for garden decoration.
Class: Floribunda.
Breeding: Seedling.
*Seed parent.*—"Baby Chateau."
*Pollen parent.*—"Contrast."
Propagation: Holds its distinguishing characteristics through succeeding propagations by budding.

*Flower*

Locality where grown and observed: Ontario, California.
Continuity: Continuous.
Fragrance: Strong. Nature—tea.
Flowers borne: Both singly and several to stem; in regular cluster; on normal stems.
Quantity of bloom: Free and abundant, both outdoors and in greenhouse.

Bud:
*Peduncle.*—Medium length; slender; erect; with numerous tiny prickles of red color. Color—reddish green.
*Before calyx breaks.*—Size—small. Form—long; pointed; globular base; with a conspicuous neck; with foliaceous appendages on the surface of the bud; with foliaceous parts extending beyond the tip of the bud equal to ½ of its length. Color—bronze green.
*As calyx breaks.*—Color—white, with marginal red color starting to show on petal edges of outer petals.
*As first petal opens.*—Size—small. Form—from globular to urn shape. Color: outside—white, with tiny yellow base spot, and with red tipped edge; inside—Strong Red, Plate 5R 4/12, terminating in white base about ½ inch long, with a tiny yellow spot at extreme end of base.
*Opening.*—Opens up well in all weather.

Bloom:
*Size (when fully open).*—Small; from 2¼ inches to 3½ inches.
*Petalage.*—Double (4 rows of petals); from 18 to 26 petals; arranged regularly.
*Form.*—Flat, open and full; petals at first being rolled outwardly, and later becoming flat and very loosely rolled outward at maturity.

Petals:
*Texture.*—Medium thick; soft. Inside—shiny-satiny. Outside—shiny-satiny.
*Shape.*—Outside—obovate; scalloped; with apex flat; with 1 notch. Intermediate—obovate; scalloped; with apex flat; with 1 notch. Inside—obovate; scalloped; with apex flat; with 1 notch.

This description of a newly opened flower was made from a rose grown outdoors during the month of October at Whittier, California:

*Color.*—Outer petal: outside surface—white, slightly margined with Strong Red, Plate 5R 4/12; inside—Strong Red, Plate 5R 4/12, with white base about ½ inch long. Intermediate petal: outside surface—white, slightly margined with Strong Red, Plate 5R 4/12; inside—Strong Red, Plate 5R 4/12, with white base about ½ inch long. Inner petal: outside surface—white, slightly margined with Strong Red, Plate 5R 4/12; inside—Strong Red, Plate 5R 4/12, with white base about ½ inch long.

This description was made from a rose that was open for three days outdoors during the month of November at La Habra, California:

*Color.*—Outer petal: outside surface—white, slightly margined with Strong Purplish Red, Plate 10RP 4/12; inside surface—Strong Purplish Red, Plate 10RP 4/12, terminating at base in ½ inch white band, with tiny yellow spot at extreme base. Inner petal: oustide surface—white, slightly margined with Strong Purplish Red, Plate 10RP 4/12; inside surface—Strong Purplish Red, Plate 10RP 4/12, terminating at base in ½ inch white band, with tiny yellow spot at extreme base.
*General color effect.*—Newly opened flower—vermilion and white contrast. 3-days open—pinking and showing white eye.
*Behavior.*—Drop off cleanly; red color intensifies as weather cools but otherwise is unaffected by weather.
*Flower longevity.*—On bush in garden—5 days in November. Cut roses grown outdoors and kept at living room temperatures—4 days throughout growing and blooming season. Cut roses grown in greenhouse and kept at living room temperature—4 days during September and October.

*Reproductive Organs*

Stamens: Many; arranged regularly about pistils. Color—golden.
Filaments: Medium length; most with anthers. Color—reddish.
Anthers: Small; open at various times. Color—yellow.
Pollen: Moderate abundance. Color—gold.
Pistils: Many.
Styles: Even; short; medium thickness; bunched.
Stigma: Color—yellow.
Ovaries: All enclosed in calyx.
Hips: Globular; smooth, walls thick and fleshy. Color—Orange Red, Plate 7.5R 4/11.
Sepals: Falling soon; moderately long; straight. Color—bronze, changing to green, with inside pubescent.
Seeds: Many; small.

*Plant*

Foliage:
*Leaves.*—Compound of 3, 5 and 7 leaflets; abundant; medium large; very leathery; glossy.
*Leaflets.*—Shape—mucronate. Base—round. Margin—simply serrate.
*Color.*—Mature: upper surface—very dark green, with high sheen; under surface—normal green and very shiny. Young: upper surface—very dark green, with high sheen; under surface—light green and shiny.
*Rachis (the supporting stem of the compound leaf).*—Light. Upper side—smooth; grooved. Under side—sparsely thorny.
*Stiples.*—Short; narrow; with moderately long points turning out at an angle more than 46°; slightly recurved toward the stem.

*Disease and insect resistance.*—Practically mildew free and good resistance to thrips and aphis, as determined by comparison with other varieties grown under comparable cultural conditions at Ontario, Whittier and La Habra, California.

Growth:
*Habit.*—Dwarf; bushy; upright; much-branched.
*Growth.*—Free; vigorous.
*Canes.*—Light.
*Main stems.*—Color—red when young, but turning bright green. Thorns—several; hooked downward; with long, narrow base. Prickles—none. Hairs—none.
*Branches.*—Color—red when young, but turning bright green. Thorns—few; short; hooked downward; with long, narrow base. Hairs—none. Prickles—none.
*New shoots.*—Color—bright red. Thorns—several; medium length; hooked downward; with long, narrow base. Prickles—none. Hairs—none.

I claim:

A new and distinct variety of rose plant of the floribunda class, substantially as herein shown and described, characterized particularly as to novelty by the unique combination of good bush form which requires no shaping or pruning, shiny, varnished deep green and clean foliage which completely clothes the plant, substantially continuous production of flowers throughout the growing season, good hardiness and long-lasting qualities of the flowers and their habit of dropping off cleanly before the flowers detract from the appearance of the plant, a distinctive and attractive vermilion-scarlet, with silvery white reverse, general color tonality of the flowers, a strong and pleasing flower fragrance, and good resistance to mildew, thrips and aphis infestations.

No references cited.